United States Patent [19]
Clausen et al.

[11] Patent Number: 5,563,040
[45] Date of Patent: Oct. 8, 1996

[54] METHOD AND APPARATUS FOR IMMUNOLOGICAL DIAGNOSIS OF FUNGAL DECAY IN WOOD

[75] Inventors: Carol A. Clausen, DeForest; Frederick Green, III, Madison, both of Wis.

[73] Assignee: The United States of America as represented by the Secretary of Agriculture, Washington, D.C.

[21] Appl. No.: 223,242

[22] Filed: Mar. 21, 1994

[51] Int. Cl.$^6$ .......................... G01N 33/53; G01N 33/569
[52] U.S. Cl. ............................ 435/7.31; 435/7.32; 435/5; 422/56
[58] Field of Search .................................. 422/56, 55, 57, 422/61; 435/5, 4, 7, 7.1, 7.31, 7.32, 7.4, 970, 971, 973, 975, 961; 436/518, 523, 528, 531, 533, 534, 169, 177, 808, 826; 530/388.5

[56] References Cited

U.S. PATENT DOCUMENTS

| | | | |
|---|---|---|---|
| 4,094,647 | 6/1978 | Deutsch et al. | 23/253 |
| 4,235,601 | 11/1980 | Deutsch et al. | 23/23 R |
| 4,361,537 | 11/1982 | Deutsch et al. | 422/56 |
| 4,943,522 | 7/1990 | Eisinger et al. | 435/7 |
| 5,047,207 | 9/1991 | Lankow et al. | 422/58 |
| 5,174,900 | 12/1992 | Nichols et al. | 210/651 |
| 5,280,078 | 1/1994 | Gregor et al. | 525/328.5 |
| 5,411,858 | 5/1995 | McGeehan et al. | 435/4 |
| 5,415,994 | 5/1995 | Imrich et al. | 435/5 |
| 5,424,193 | 6/1995 | Pronovost et al. | 435/7.32 |

FOREIGN PATENT DOCUMENTS

| | | |
|---|---|---|
| 0250137 | 12/1987 | European Pat. Off. . |
| 0291194 | 11/1988 | European Pat. Off. . |

OTHER PUBLICATIONS

Clausen, C. A., Green III, F & Highley, T. L. "Characterization of Monoclonal Antibodies to Wood–Derived β–1, 4–xylanase of *Postia placenta* & their application to detection of Incipient Decay," *Wood Science & Technology* (27:219–228, 1993).

Clausen, C. A., Green III, F & Highley T. L., "Early Detection of Brown–Rot Decay in Southern Yellow Pine Using Monoclonal Antibodies" In: Rossmoore, H. W., ed. Biodeterioration & Biodegradation 8: Proc. of the 8th Int'l Biodet. & Biodeg. Symposium; 1990 Aug. 26–31; Windso, On Canada, New York: Elsevier Applied Science; 1991: 412–414.

Clausen, C. A., "Enzyme Immunoassay to Detect *Postia placenta* in Field Tests Comparison of plate ELISA with Hydrophobic Cloth & Cotton Dipsticks," The Int'l Research Group on Wood Preservation 22nd Annual Mtg. Mar. 21, 1991 Doc. No. IRE/WP/2378, 8 pgs.

Clausen, C. A. Green III, F & Highley, T. L., "Cross–blot: A Rapid Screening Procedure for Determining Specificity of Antibodies to Native Proteins of the Brown–Rot fungus *Postia placenta*", FEMS Microbiology Letters, 78 (1991) 315–318.

*Primary Examiner*—James C. Housel
*Assistant Examiner*—Ginny Allen Portner
*Attorney, Agent, or Firm*—Janet I. Stockhausen; M. Howard Silverstein; John D. Fado

[57] ABSTRACT

A method and apparatus for detecting incipient fungal decay in wood is described. Anti-xylanase monoclonal antibody is immobilized in a defined capture zone to a polyester assay substrate. Anti-hemicellulase polyclonal-labeled latex particles (carrier zone) are applied at a position distant from the capture zone. Wood extract to be tested is applied to the end of the polyester substrate and allowed to flow laterally through the carrier zone and the capture zone. A positive test results when antigen in the wood extract is complexed by the labeled polyclonal and monoclonal antibodies to form an observable particle complex.

14 Claims, 1 Drawing Sheet

U.S. Patent
Oct. 8, 1996
5,563,040
FIG. 1
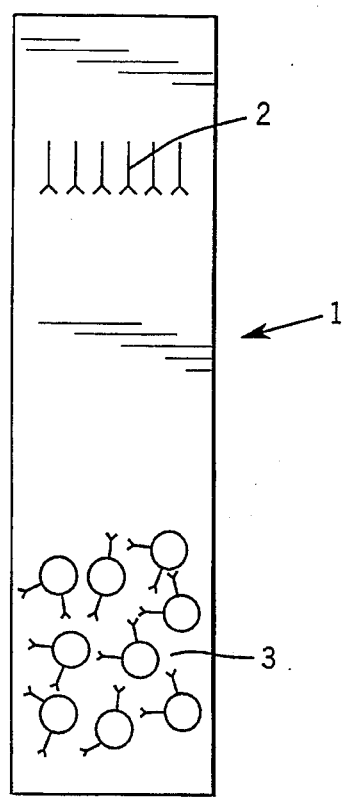
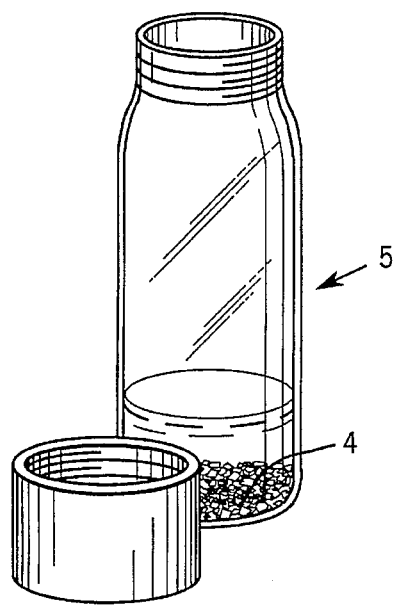
FIG. 2A
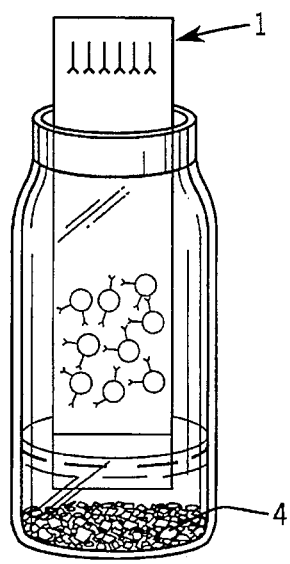
FIG. 2B
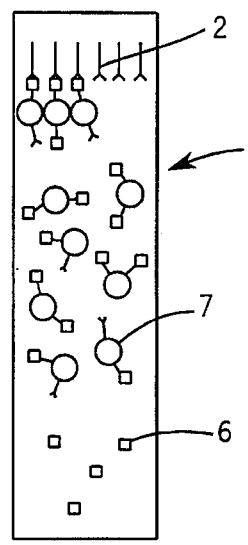
FIG. 2C
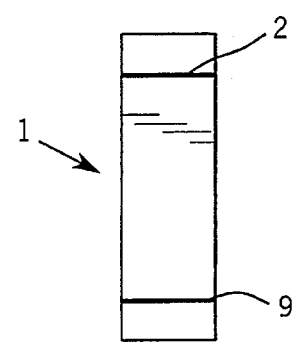
FIG. 2D

METHOD AND APPARATUS FOR IMMUNOLOGICAL DIAGNOSIS OF FUNGAL DECAY IN WOOD

BACKGROUND OF THE INVENTION

This invention relates to the diagnosis of fungal decay in wood. In one aspect, the invention relates to a method especially well suited for the field diagnosis of infected in-service wood by incipient fungal decay. In yet another aspect, the invention relates to an apparatus useful in performing that method.

The microbiological deterioration of wood is very serious because it can cause structural failure. Wood that has lost only 3% of its weight because of decay will frequently exhibit a 50% loss in strength measured as toughness (Kennedy, 1958, Richards and Chidester, 1940). Many types of microorganisms deteriorate wood, but the greatest damage is caused by fungi. The most important wood-degrading fungi are white- and brown-rot fungi. White-rot fungi are most commonly found in the forest, while brown-rot decay is the most common type of decay in wood products "in-service". Brown-rot decay is also the most destructive.

Detection of decay in wood structures, particularly in the early stages, has long been a major problem. Sounding of wood, visual or microscopic inspection of borings from wood, radiography, sonics and various mechanical probing devices are useful for detecting advanced decay. However, early stages of decay are often difficult to detect with these methods. For detection of early decay, application of chemical indicators to core samples has shown some promise but results are often not clear or difficult to interpret. An electronic-type detector, the Shigometer™, has been used for detection of early internal decay in trees and utility poles. However, this instrument appears to give unreliable results when used with wood products. Misdiagnosis can lead to unnecessary replacement of uninfected wood or inappropriate remedial treatments prior to structural compromise which inevitably precedes morphological changes.

Numerous comparatively simple and inexpensive diagnostic tests have been successfully developed using antibodies to detect human and animal diseases in very early stages of infection. To do this, a first antibody, which is reactive with a selected antigen that is, or is associated with, a disease causing organism, may be immobilized on a solid support member; and then a sample liquid solution, which is suspected of harboring the selected antigen, is contacted with the immobilized antibody. If the selected antigen is present in the sample liquid solution, the antigen reacts with and becomes bound to the first antibody to form an antigen-antibody binary complex on the solid support member.

After washing the unreacted material from the support member, the binary complex is contacted with a second, labeled antibody that is also reactive with the selected antigen. If the binary complex is present on the solid support, this second antibody reacts with and becomes bound to the antigen component of the complex to form an antibody-antigen-antibody tertiary complex. After washing the solid support member to remove any of the second antibody that did not react with the selected antigen, the support member is tested for the second antibody by any of a variety of analytical techniques.

Diagnostic procedures of the above-outlined type have been successfully developed using polyclonal and monoclonal antibodies to detect antigens associated with particular diseases with a very high degree of reliability. Monoclonal antibodies are made via a process, referred to as hybridoma technology, in which hybridomas are formed by the fusion of short-lived antibody producing cells (usually spleen cells) and long-lived myeloma cells to produce long-lived antibody synthesizing cell lines. Each hybrid cell line produces a unique and characteristic antibody that has the ability to bind, with a very high degree of specificity, to a single type of antigen.

The cells that are fused to form a particular hybridoma cell line can be selected or treated so that the monoclonal antibody synthesized by that cell line will bind only to a chosen antigen. If such an antibody is used in the above-discussed procedure as either the first or second antibody, then the antibody-antigen-antibody tertiary complex will form on the solid support member, with a very high degree of accuracy, if and only if the chosen antigen is present in the sample liquid solution. Polyclonal antibodies with the appropriate affinity and specificity may also be used to detect antigens with a very high degree of accuracy.

Procedures of the above-outlined general type have been successfully employed on a commercial basis in the laboratory to test for human and animal diseases, among other things. Because of the relative simplicity and accuracy of procedures of this type, it would be very desirable to provide similar tests to diagnose wood decay. Unique problems, however, have been encountered in developing commercially practical procedures, of the above-discussed general type, for the field diagnosis of fungal infection in wood. Previous immunodiagnostic methods for the detection of fungal infection in wood were based on enzyme-linked immunosorbent assays which require laboratory testing with expensive equipment and scientific expertise. Furthermore, past attempts to utilize monoclonal antibodies and polyclonal antibodies to fungal components for detecting fungal infection in wood have been fraught with high background and non-specific reactions, mostly due to the lack of antibody specificity.

SUMMARY OF THE INVENTION

In one embodiment of this invention, we have discovered a method especially well suited for the field diagnosis of infected in-service wood by a group of Basidiomycetes responsible for brown-rot decay. In another embodiment of this invention, we have developed an apparatus useful in performing the method.

The apparatus of the present invention comprises a polyester support with a carrier zone and at least one capture zone. The carrier zone comprises antibody-coated latex particles. The capture zone comprises an antibody bound to the surface of the polyester support.

Samples of wood extract to be tested are applied to the carrier zone end of the polyester substrate and allowed to flow through the substrate to the capture zone. Fungal antigens bind to the antibody-coated latex beads and are carried on the beads to the capture zone. In the capture zone, the bead-bound antigens form an observable particle complex with the capture antibody which is passively bound to the polyester substrate, i.e. a visible color change.

BRIEF DESCRIPTION OF THE DRAWINGS

FIG. 1 is a schematic depiction of one embodiment of the apparatus useful in this invention.

FIG. 2A, 2B, 2C, and 2D is a schematic flow diagram of one embodiment of the method of this invention. FIG. 2A depicts a wood sample 4 placed in a sample vial 5 containing extraction fluid, FIG. 2B describes the testing of the wood extract solution for the suspended antigen by contacting the liquid with pre-coated polyester support 1, FIG. 2C describes specific antigen 6 in the sample attaching to polyclonal-labelled beads 7 and moving laterally through polyester support 1 to capture zone 2 as the extract is wicked upward, and FIG. 2D illustrates a positive reaction in which a colored line is visible in capture zone 2. A second colored line, 9, merely represents residual coated polystyrene beads.

DETAILED DESCRIPTION OF THE INVENTION

In accordance with the present invention, and with reference to FIG. 1, polyester substrate 1 is coated with at least one antibody at capture zone 2 and antibody-coated carrier body at the carrier zone 3. As used herein, the terms "polyester substrate" and "polyester support" can be used interchangeably to refer to the apparatus described in this invention. Preferably, the polyester substrate comprises hydrophobic polyester cloth. As used herein, the term "polyester cloth" refers to a semi-rigid, fibrous, cloth-like material comprising the polyester substrate. Further, the hydrophobic nature of the polyester cloth is required to permanently immobilize the antibody to capture zone 2. The invention did not work when the support was comprised of nitrocellulose due to nonspecific binding of the latex beads. The length and width of the polyester cloth is based on a factor of economy and convenience. The antibodies used in the capture and carrier zones can be comprised of monoclonal antibodies, polyclonal antibodies and mixtures thereof. In one embodiment, capture zone 2 of FIG. 1 is comprised of a purified anti-xylanase monoclonal antibody which is immobilized onto one end of polyester substrate 1. Monoclonal antibodies utilized in the practice of this invention may be made or obtained in any suitable manner. For example, Clausen, Green and Highley describe a method of preparing and purifying murine monoclonal antibodies to the extracellular $\beta$-1,4-xylanase fraction of the brown-rot fungus, *Postia placenta* in "Characterization of Monoclonal Antibodies to Wood-Derived -1,4-Xylanase of *Postia placenta* and Their Application to Detection of Incipient Decay", Wood Science and Technology, August 1991 which is herein incorporated in its entirety.

Carrier zone 3 of FIG. 1 is comprised of a polyclonal antibody complex which is applied to the polyester substrate 1 opposite capture zone 2. The distance between the capture and carrier zones is based on the characteristics of the specific polyester substrate. Optimally, the distance between the zones is such that the reaction between the suspected antigen and the antibodies is maximized without agglutination of the carrier body during migration toward the capture zone. Typically, the zones will be located at a distance of between about 3 to 5 cm from one another, preferably a distance of about 4 cm. The polyclonal antibody complex is comprised of a polyclonal antibody bound to a carrier body. Preferably, the carrier body is comprised of polystyrene beads, even more preferably colored polystyrene beads.

The capture zone is comprised of at least one capture antibody. The maximum number of capture zones is a function of the total distance between the capture and carrier zones. As mentioned above, the distance between the capture and carrier zones is such that the reaction between the suspected antigen and the antibodies is maximized without agglutination of the carrier body. Typically, the polyester substrate can support at least one but no more than five capture zones.

Polyester support 1 is prepared by first passively binding the anti-xylanase monoclonal antibody to the hydrophobic polyester cloth in a line at one end of the polyester cloth. The antibody is dried on the polyester substrate at any suitable temperature, e.g. 40° C. In order to avoid non-specific binding reactions, the entire polyester support is saturated with sucrose/bovine serum albumin (BSA) mixture and dried before the application of the polyclonal-labeled beads.

Polyclonal antibody is passively adsorbed to polystyrene beads. Preferably, the antibody is adsorbed to colored polystyrene beads; however white beads can also be used if an enzyme conjugate is included which reacts with a selected enzyme substrate to produce a product having a particular color (the use of colored polystyrene beads eliminates this additional step). The polyclonal-labeled colored beads are applied to the coated polyester support in a line approximate and opposite the capture zone and dried as previously described. The dried coated polyester supports are preferably stored at about 0°–10° C.

A preferred procedure for carrying out the method of the present invention is depicted in FIG. 2. In FIG. 2A, a wood sample 4 is placed in a sample vial 5 containing extraction fluid. As used herein, the term "wood sample" refers to any sample, such as a wood chip, sawdust, wood pulp or wood meal, which is preferentially homogeneous in nature in that it is representative of an entire core boring. However, any wood sample may be tested. The extraction fluid typically contains water with 0.1% TRITON X-100, a surfactant which solubilizes fungal membranes releasing fungal antigens. To ensure adequate extraction of the suspected antigen, the wood sample is allowed to soak in the extraction fluid for at least about one hour. The solution is then tested for the presence of the suspected antigen.

In FIG. 2B, the wood extract solution is tested for the suspected antigen by contacting the liquid with precoated polyester support 1. The test is preferably performed at about 20°–30° C. As FIG. 2C illustrates, specific antigen 6 in the sample attaches to polyclonal-labeled beads 7 and moves laterally through polyester support 1 to capture zone 2 as the extract is wicked upward. Specific antigen attached to the polyclonal-labeled beads is captured by the immobilized monoclonal to form a line of colored latex beads indicating a positive reaction.

Once polyester support 1 is saturated with the sample, it is carefully washed or rinsed after being removed from the wood extract solution to remove the unreacted reactants from the antibody complex. In a positive reaction, as illustrated in FIG. 2D, a colored line will be easily visible in capture zone 2 because the antigen is sandwiched between the polyclonal antibody-labeled bead and the monoclonal antibody. A second colored line is also present in the carrier zone 3 of the polyester support. This colored line, however, merely represents the residual coated polystyrene beads 9. In a negative test, the polyclonal antibody-labeled beads pass through the capture zone and no colored line results in capture zone 2. The only colored line present on the polyester support is the one in the carrier zone 3 which, as described above, represents the residual coated polystyrene beads 9.

If desired, a test may be done using the above-described procedure except that no wood sample would be added to the extraction fluid. Such a negative control test may be desirable to determine if the test procedure is being properly performed, and to indicate the extent, if any, to which the polyester support will turn a particular color by means other than a reaction with the antibody-suspected antigen-capture antibody complex. A positive control test using a liquid solution known to contain the suspected antigen at an appropriate concentration, can be done to ensure that the antigen can be detected on the polyester substrate. Moreover, a positive control test may incorporate an additional capture zone comprised of an anti-antibody zone which is capable of trapping the coated polystyrene bead to the capture zone.

The method of this invention is relatively simple and may be carried out by an individual without elaborate training or instructions. Also, the method is very easy to perform in the field, and does not require any expensive heavy or cumbersome equipment other than a sample vial, the polyester substrate, extraction fluid and the wood sample.

Numerous modifications and embodiments devised by those skilled in the art other than the ones specifically described above, may be employed to detect the presence of the suspected antigen. For instance, antibodies to other fungal components or other groups of fungi (e.g. sapstain fungi or white-rot fungi) can alteratively be used in this invention. Moreover, there is no absolute requirement that the capture zone be comprised of monoclonal antibodies and that the carrier zone be comprised of polyclonal-labeled polystyrene beads. Monoclonal antibodies and polyclonal antibodies can be used interchangeably in both zones of the polyester substrate. Moreover, there is no absolute requirement that different antibodies be used in both zones of the polyester substrate; it is possible to utilize the same antibody in both the capture and carrier zones.

Alternate designs are also available for the described dyed particle capture immunoassay. For example, one can incorporate monoclonal antibody-labeled white latex particles in the capture zone of the test strip. Additionally, white polystyrene beads can be used as the carrier body if an enzyme conjugate is included which reacts with a selected enzyme substrate to produce a product having a particular color.

The invention is further described by the following Specific Embodiments.

SPECIFIC EMBODIMENTS

EXAMPLE 1

A. Preparation of Murine Monoclonal Antibodies

The method for preparing murine monoclonal antibodies to the extracellular β-1,4-xylanase fraction of the brown-rot fungus, *Postia placenta* is described by Carol A. Clausen, Frederick Green III and Terry L. Highley in an article entitled "Characterization of Monoclonal Antibodies to Wood-Derived β-1,4-Xylanase of *Postia placenta* and Their Application to Detection of Incipient Decay", Wood Science and Technology, Aug. 1991.

Specifically, antigen was prepared by inoculating Southern yellow pine (Pinus sp.) wood blocks with *Postia placenta* and incubating them at 27° C. for 9 weeks. An extract was prepared by grinding the decayed wood blocks in phosphate-buffered saline (PBS), 0.1% Triton X-100 (Sigma, St. Louis, Mo.), 0.85% NaCl, pH 7.2, and filtering the homogenate through cheesecloth. The resulting extract was dialyzed, ultracentrifuged at 128,000×g for 2 hours, and passed sequentially through Sepharose 6B (Pharmacia, Piscataway, N.J.) and Fractogel TSK HW-55 (F) (EM Science, Gibbstown, N.J.) columns, both equilibrated with PBS, pH 7.2. Chromatography fractions were eluted in PBS, and those eluants containing xylanase activity served as antigen.

Six-week-old female BALB/c mice were immunized intraperitoneally (IP) with 10 micrograms protein per 0.5 ml in 50% Freund's complete adjuvant, and boosted IP at two week intervals with the same antigen in PBS. Mice were bled at 4 weeks and their serum was tested by enzyme linked immunosorbent assay (ELISA) (Stahli, et al., 1983). Five days prior to the fusion, the mouse with the highest titer was inoculated intravenously (IV) with 0.1, and IP with 0.5 on two successive days prior to fusion. The spleen was surgically removed and collected splenocytes were fused with $10^7$ NS-1 myeloma cells. Fused cells were suspended in Dulbecco's Modified Eagle's Minimal Essential Medium (DME)(Gibco), hypoxanthine, aminopterin and thymidine and plated in sterile 96-well cell culture plates. Hybridomas were selected by ELISA and western blot. Dilution cloning of the hybridomas yielded five clones from different colonies. Monoclonal antibodies were isotyped using a commercially available kit utilizing an Ouchterlony assay (Binding Site, San Diego, Calif.). The monoclonal antibodies were characterized as specific for hemicellulases of *Postia placenta* with affinity chromatography.

B. Preparation of Polyclonal Antibody

P. placenta-decayed sweetgum (*Liquidambar styraciflua*) was extracted in 50 mM Tris, 0.85% NaCl, and 0.1 mM EDTA, pH 7.0, and ultracentrifuged at 36,000×g for 2 h. Hemicellulases were fractionated by passing through a 60-× 2-cm Sepharose 6B (Pharmacia, Piscataway, N.J.) column equilibrated with 50 mM Tris-HCl buffer and subsequently passed through a 90-×26-cm Fractogel TSK HW-55 (F) (EM Science, Gibbstown, N.J.) column equilibrated with 50 mM Tris-HCl buffer, pH 7.0, 0.5 NaCl. Fractions containing hemicellulase activity as determined by the microadaptation of the Nelson-Somogyi reducing sugar assay were pooled, dialyzed, mixed 1:1 with Freund's Complete Adjuvant (Difco, Detroit, MI), and injected subcutaneously at multiple sites in New Zealand white rabbits. At 30 days post-inoculation, rabbits were boosted intramuscularly with hemicellulase: Freund's Incomplete Adjuvant (Difco) and bled 7–10 days later.

C. Preparation of the Coated Polyester Support

Anti-xylanase monoclonal antibody (twenty microliters of 1.0 mg/ml protein concentration) was passively bound to the hydrophobic polyester cloth in a 0.2×1 cm line, 4 cm from the end of a 1×6 cm strip of polyester cloth (Sontara No. 8100, E I DuPont Nemours & Co., Wilmington, Del.). The antibody was dried on the polyester support at 40° C. The entire polyester support was then saturated with 10% sucrose and 0.2% bovine serum albumin (BSA) in water for 1 hour at 25° C., dried at 40° C., recoated with the sucrose/BSA mixture, then completely dried at 40° C.

Polyclonal antibody was passively adsorbed to colored polystyrene beads (0.7–0.8 μm in diameter). Colored polystyrene beads (Seradyn, Indianapolis, Ind.) (twenty microliters), labeled with polyclonal antibody, at 2–3% solids by weight were applied to the coated polyester support in a 0.2×1 cm line 1 cm from the bottom of the polyester support and dried at 40° C.

D. Test Procedure

Wood extract for testing was prepared by soaking a wood sample comprising wood shavings at a ratio of 50–100 mg/ml in water with 0.1% TRITON X-100 (Sigma Chemical, St. Louis, Mo.) for 2 hours at 20°–30° C. Pre-coated polyester supports were then dipped into the wood extract. As the extract was wicked upward, any specific antigen in the sample attaches to the polyclonal-labeled beads and moves laterally through the polyester substrate to the capture zone comprised of the antixylanase monoclonal antibody. In a positive test, the antigen is sandwiched between the polyclonal antibody-labeled bead and the monoclonal antibody, and an easily visible colored line will result in the capture zone, 4 cm from the bottom of the polyester substrate. In a negative test, the polyclonal antibody-labeled beads pass through the capture zone and no colored line results.

The method detailed above was carried out on various known fungal antigens. The dyed particle capture immunoassay described above was able to detect six of the most aggressive brown-rot fungi at less than 2% wood weight loss (*Serpula incrassata*, 0.8%, *Lentinus lepideus*, 0%, *Postia placenta*, 0.4% *Antrodia carbonica*, 0.4%, *Coniophora puteana*, 1.1%, and *Gloeophyllum trabeum*, 1.9%).

The foregoing description and examples are for the purpose of illustration only, and does not limit the scope of protection which should be accorded this invention.

What is claimed is:

1. A polyester assay device for detecting fungal decay in wood, the device comprising:
   A) a hydrophobic polyester cloth substrate;
   B) at least one capture zone comprising immobilized capture antibodies specific for a fungal antigen, said capture antibodies being immobilized on the polyester cloth substrate, wherein the fungal antigen originates from a fungus known to cause fungal decay; and
   C) a carrier zone, spaced from said capture zone, to which a sample is directly applied, comprised of carrier antibodies bound to mobile polystyrene beads, wherein the carrier antibodies specifically bind said antigen and wherein binary immune complexes are formed between the carrier antibodies and said antigen resulting in antigen/carrier antibody/polystyrene bead complexes, said complexes being disposed within the polyester cloth, and;
   wherein said complexes migrate through the cloth to contact the capture zone and form tertiary immune complexes with the capture antibodies.

2. The substrate of claim 1 in which the capture zones do not exceed five in number.

3. The substrate of claim 1 in which the capture antibody is selected from the group consisting of a monoclonal antibody, a polyclonal antibody and mixtures thereof.

4. The substrate of claim 3 in which the capture antibody is specific for an antigen from Basidiomycete fungi.

5. The substrate of claim 4 in which the Basidiomycete fungi are responsible for brown-rot decay.

6. The substrate of claim 5 in which the Basidiomycete fungus is *Postia placenta*.

7. The substrate of claim 6 in which the capture antibody is an anti-xylanase monoclonal antibody.

8. The substrate of claim 1 in which the carrier antibody is selected from the group consisting of a monoclonal antibody, a potyclonal antibody and mixtures thereof.

9. The substrate of claim 8 in which the carrier antibody is an anti-hemicellulase polyclonal antibody.

10. A polyester assay device for detecting fungal decay in wood, the device comprising:
    A) a hydrophobic polyester cloth substrate;
    B) at least one but not more than five capture zones, wherein at least one capture zone comprises immobilized anti-xylanase monoclonal antibodies immobilized on the polyester cloth substrate which specifically bind an antigen from Postia placenta; and
    C) a carrier zone, spaced from said capture zone, to which a sample is directly applied, comprised of carrier antibodies bound to mobile polystyrene beads, wherein the carrier antibodies specifically bind said antigen and wherein binary immune complexes are formed between the carrier antibodies and said antigen resulting in antigen/carrier antibody/polystyrene bead complexes, said complexes being disposed within the polyester cloth, and;
    wherein said complexes migrate through the cloth to contact the capture zone and form tertiary immune complexes with the capture antibodies.

11. A method for detecting fungal decay in wood, the method comprising:
    A) placing a wood sample in an aqueous fluid, wherein a fungal antigen is extracted into the fluid;
    B) contacting the resulting solution with a hydrophobic polyester cloth device wherein the device comprises at least one capture zone comprising immobilized capture antibodies specific for a fungal antigen, said antibodies being immobilized on the polyester cloth, wherein the fungal antigen originates from a fungus known to cause fungal decay; and a carrier zone, spaced from said capture zone, comprised of carrier antibodies bound to mobile polystyrene beads, wherein the carrier antibodies specifically bind said antigen, said beads being disposed within the polyester cloth, wherein binary immune complexes are formed between the carrier antibodies and the antigen resulting in antigen/carrier antibody/polystyrene bead complexes;
    C) allowing the said complexes to migrate through the polyester cloth to the at least one capture zone, contacting the capture antibodies, wherein tertiary immune complexes are formed between the binary complexes and the capture antibodies, and
    D) visually observing the tertiary complexes.

12. A kit for detecting fungal decay in wood, the kit comprising:
    A) a sample vial;
    B) aqueous fluid; and
    C) a hydrophobic polyester cloth device to which a sample is directly applied, wherein the substrate comprises at least one capture zone comprising immobilized capture antibodies specific for a fungal antigen wherein the fungal antigen originates from a fungus known to cause fungal decay and a carrier zone spaced from said capture zone, comprised of carrier antibodies bound to mobile polystyrene beads, wherein the carrier antibodies specifically bind said antigen.

13. The kit of claim 12 in which the extraction fluid comprises water and TRITON X-100 surfactant.

14. The kit of claim 13 in which the extraction fluid comprises 0.1% TRITON X-100 surfactant.

* * * * *